US00PP23789P2

(12) United States Plant Patent
Geibel

(10) Patent No.: US PP23,789 P2
(45) Date of Patent: Jul. 30, 2013

(54) GERANIUM PLANT NAMED 'REGDAR'

(50) Latin Name: *Pelargonium grandiflorum*
Varietal Denomination: Regdar

(75) Inventor: Martin Geibel, Dresden (DE)

(73) Assignee: Elsner PAC Jungpflanzen, Dresden (DE)

( * ) Notice: Subject to any disclaimer, the term of this patent is extended or adjusted under 35 U.S.C. 154(b) by 374 days.

(21) Appl. No.: 12/931,670

(22) Filed: Feb. 7, 2011

(51) Int. Cl.
*A01H 5/00* (2006.01)

(52) U.S. Cl.
USPC ..... Plt./331

(58) Field of Classification Search
USPC ..... Plt./331
See application file for complete search history.

(56) References Cited

U.S. PATENT DOCUMENTS

PP20,426 P2 * 10/2009 Michalik ..... Plt./331
PP20,655 P2 * 1/2010 Michalik ..... Plt./331
PP22,908 P2 * 7/2012 Geibel ..... Plt./324

OTHER PUBLICATIONS

UPOV ROM database, GTI Jouve retrieval software citation for 'Regdar'. Apr. 15, 2010.*
PLUTO citations for 'Regdar' Jun. 2012.*

* cited by examiner

*Primary Examiner* — Wendy C Haas
(74) *Attorney, Agent, or Firm* — C. A. Whealy

(57) ABSTRACT

A new and distinct cultivar of Regal Geranium plant named 'Regdar', characterized by its upright, somewhat outwardly spreading and uniformly mounded plant habit; vigorous growth habit; freely basal branching habit; early and freely flowering habit; dark purple, red purple and light red purple-colored flowers; and ability to initiate and develop flowers without a cooling treatment.

1 Drawing Sheet

Botanical designation: *Pelargonium grandiflorum.*
Cultivar denomination: 'REGDAR'.

BACKGROUND OF THE INVENTION

The present invention relates to a new and distinct cultivar of Regal Geranium plant, botanically known as *Pelargonium grandiflorum*, and hereinafter referred to by the name 'Regdar'.

The new Regal Geranium plant is a product of a planned breeding program conducted by the Inventor in Dresden, Germany. The objective of the breeding program is to develop new early flowering Regal Geranium plants that do not require a cooling treatment for flower development.

The new Regal Geranium plant originated from a cross-pollination made by the Inventor in Dresden, Germany during the summer of 2005 of two unnamed proprietary selections of *Pelargonium grandiflorum,* not patented. The new Regal Geranium plant was discovered and selected by the Inventor as a flowering plant from within the progeny of the stated cross-pollination in a controlled greenhouse environment in Dresden, Germany during the spring of 2006.

Asexual reproduction of the new Regal Geranium plant by vegetative terminal cuttings in a controlled greenhouse environment in Dresden, Germany since October, 2006 has shown that the unique features of this new Regal Geranium plant are stable and reproduced true to type in successive generations.

SUMMARY OF THE INVENTION

Plants of the new Regal Geranium have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Regdar'. These characteristics in combination distinguish 'Regdar' as a new and distinct Regal Geranium plant:

1. Upright, somewhat outwardly spreading and uniformly mounded plant habit.
2. Vigorous growth habit.
3. Freely basal branching habit.
4. Early and freely flowering habit.
5. Dark purple, red purple and light red purple-colored flowers.
6. Does not require cooling treatment for flower development.

Plants of the new Regal Geranium differ primarily from plants of the parent selections in flower coloration. In addition, plants of the new Regal Geranium are more uniform than plants of the parent selections.

Plants of the new Regal Geranium can be compared to plants of the *Pelargonium grandiflorum* 'Cambi', disclosed in U.S. Plant Pat. No. 20,426. In side-by-side comparisons conducted in Dresden, Germany, plants of the new Regal Geranium differed from plants of 'Cambi' in the following characteristics:

1. Plants of the new Regal Geranium were not as outwardly spreading as plants of 'Cambi'.
2. Plants of the new Regal Geranium had larger flowers than plants of 'Cambi'.
3. Plants of the new Regal Geranium and 'Cambi' differed in flower color as plants of 'Cambi' had red purple and pale purple bi-colored flowers.

4. Flowers of plants of the new Regal Geranium had larger sepals than flowers of plants of 'Cambi'.

Plants of the new Regal Geranium can also be compared to plants of the *Pelargonium grandiflorum* 'Camstra', disclosed in U.S. Plant Pat. No. 22,908. In side-by-side comparisons conducted in Dresden, Germany, plants of the new Regal Geranium differed from plants of 'Camstra' in the following characteristics:

1. Plants of the new Regal Geranium had larger flower umbels than plants of 'Camstra'.
2. Plants of the new Regal Geranium and 'Camstra' differed in flower color.
3. Lower petals of flowers of plants of the new Regal Geranium were shorter than lower petals of flowers of plants of 'Camstra'.

BRIEF DESCRIPTION OF THE PHOTOGRAPH

The accompanying colored photograph illustrates the overall appearance of the new Regal Geranium plant showing the colors as true as it is reasonably possible to obtain in colored reproductions of this type. Colors in the photograph may differ slightly from the color values cited in the detailed botanical description which accurately describe the colors of the new Regal Geranium plant.

The photograph comprises a side perspective view of a typical flowering plant of 'Regdar' grown in a container.

DETAILED BOTANICAL DESCRIPTION

The aforementioned photograph and following observations, measurements and values describe plants grown during the winter and spring in 13-cm containers in a glass-covered greenhouse in Dresden, Germany and under conditions which closely approximate commercial Regal Geranium production. During the production of the plants, day temperatures averaged 18° C., night temperatures averaged 16° C. and light levels ranged from 15 kilolux to 100 kilolux. Plants were six months old when the photograph and the description were taken. In the detailed description, color references are made to The Royal Horticultural Society Colour Chart, 1995 Edition, except where general terms of ordinary dictionary significance are used.

Botanical classification: *Pelargonium grandiflorum* 'Regdar'.

Parentage:

*Female, or seed, parent*.—Unnamed proprietary selection of *Pelargonium grandiflorum*, not patented.

*Male or pollen parent*.—Unnamed proprietary selection of *Pelargonium grandiflorum*, not patented.

Propagation:

*Type*.—By vegetative terminal cuttings.

*Time to initiate roots, summer*.—About 18 days at temperatures of 20° C.

*Time to initiate roots, winter*.—About 22 days at temperatures of 20° C.

*Time to produce a rooted young plant, summer and winter*.—About one month at temperatures of 20° C.

*Root description*.—Fine, fibrous; white in color.

*Rooting habit*.—Freely branching; dense.

Plant description:

*Plant and growth habit*.—Upright, somewhat outwardly spreading and uniformly mounded plant habit; inverted triangle; densely foliated; vigorous growth habit; freely basal branching habit with about 15 lateral branches developing per plant.

*Plant height, to top of umbels*.—About 25 cm.

*Plant height, to top of leaves*.—About 20 cm.

*Plant width*.—About 40 cm.

*Lateral branches*.—Length: About 8 cm. Diameter: About 5 mm. Internode length: About 2 cm. Texture: Moderately pubescent. Color: Close to 144A.

Foliage description:

*Arrangement*.—Alternate or opposite; simple.

*Length*.—About 5 cm.

*Width*.—About 6 cm.

*Shape*.—Cordate; palmately lobed.

*Apex*.—Acute.

*Base*.—Cordate, open.

*Margin*.—Serrate.

*Venation pattern*.—Palmate.

*Texture, upper surface*.—Rough, glabrous; leathery.

*Texture, lower surface*.—Slightly pubescent along veins.

*Color*.—Developing leaves, upper and lower surfaces: Close to 144A. Fully expanded leaves, upper surface: Close to 137B; venation, close to 137B. Fully expanded leaves, lower surface: Close to 147B; venation, close to 147C. Zonation pattern: Not discernible. Petiole: Length: About 3 cm to 5 cm. Diameter: About 2 mm. Texture, upper and lower surfaces: Slightly pubescent. Color, upper and lower surfaces: Close to 146A.

Flower description:

*Flower arrangement and flowering habit*.—Single rotate flowers arranged in inversely conical umbels arising from apical leaf axils; umbels displayed above the foliar plane on strong peduncles; flowers face upright to outward; freely flowering habit; about five flowers per umbel.

*Fragrance*.—None detected.

*Flowering season*.—Early flowering habit, plants begin flowering about five months after planting; in Germany, flowering begins in April and continues until October; plants do not require a cooling treatment for flower initiation and development.

*Flower longevity*.—Flowers last about two weeks on the plant; flowers not persistent.

*Umbel height*.—About 6 cm.

*Umbel diameter*.—About 10 cm.

*Flower diameter*.—About 5 cm.

*Flower depth (height)*.—About 3 cm.

*Flower buds*.—Length: About 1.5 cm. Diameter: About 5 mm. Shape: Spindle-shaped. Color: Close to 146B.

*Petals*.—Quantity per flower: Five arranged in a single whorl; petals imbricate. Length, upper two petals: About 3.7 cm. Length, lower three petals: About 3.3 cm. Width, upper two petals: About 3.3 cm. Width, lower three petals: About 2.2 cm. Shape: Obovate. Apex: Rounded. Base: Cuneate. Margin: Entire. Texture, upper and lower surfaces: Smooth, glabrous; satiny. Color, upper two petals: When opening and fully opened, upper surface: Center, close to 187A; towards the margin, close to 60A; at the margin, close to 62A; towards the base, close to 155D; venation, close to 187A; color becoming closer to 62A with development. When opening and fully opened, lower surface: Center, close to 187A; towards the margin, close to 60A; at the margin, close to 62A; towards the base, close to 155D; venation, close to 58A. Color, lower three petals: When opening and fully opened, upper surface: Close to 62A; towards the base, close to 155D; venation, close to 187A; color becoming closer to 155D with development. When opening and fully opened, lower surface: Close to 62D; towards the base, close to 155D; venation, close to 58A.

*Sepals*.—Quantity per flower: Five arranged in a single whorl. Length: About 1.8 cm. Width: About 5 mm. Shape: Lanceolate. Apex: Acute. Margin: Entire. Texture, upper and lower surfaces: Pubescent. Color, upper and lower surfaces: Close to 144A.

*Peduncle* (*umbel stem*).—Length: About 4.5 cm. Diameter: About 2 mm. Strength: Strong. Angle: Mostly erect to slightly outwardly slanted. Texture: Moderately pubescent. Color: Close to 146B.

*Pedicel* (*individual flower stem*).—Length: About 2 cm. Diameter: About 1 mm. Strength: Strong; flexible. Texture: Moderately pubescent. Color: Close to 146B.

*Reproductive organs*.—Androecium: Stamen quantity per flower: About ten. Anther length: About 2 mm. Anther shape: Tubular. Anther color: Close to 179A. Pollen amount: Abundant. Pollen color: Close to 167A. Gynoecium: Pistil quantity per flower: One. Pistil length: About 1.7 cm. Stigma shape: Five to seven-parted. Stigma color: Close to 59A. Style length: About 1 cm. Style color: Close to 59D. Ovary color: Close to 147C. Seeds and fruits: Seed and fruit development have not been observed on plants of the new Regal Geranium.

Disease/pest resistance: Plants of the new Regal Geranium have not been observed to be resistant to pathogens and pests common to Regal Geraniums.

Temperature tolerance: Plants of the new Regal Geranium have been observed to tolerate temperatures ranging from about 1° C. to about 35° C. to 40° C.

It is claimed:

1. A new and distinct Regal Geranium plant named 'Regdar' as illustrated and described.

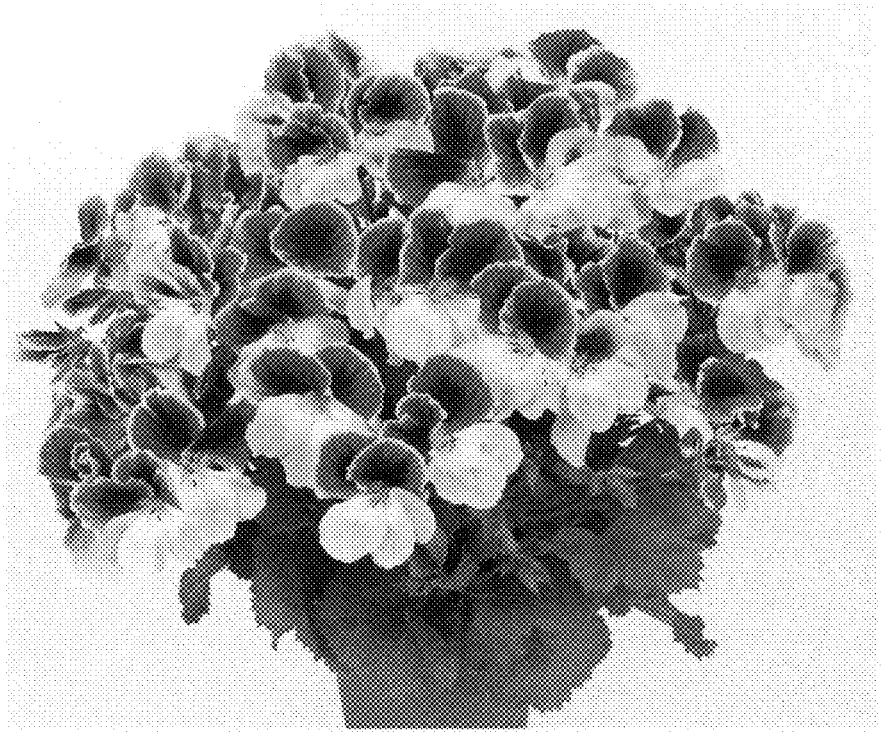

* * * * *